(12) United States Patent
Halsmer et al.

(10) Patent No.: US 6,895,076 B2
(45) Date of Patent: May 17, 2005

(54) METHODS AND APPARATUS FOR MULTIPLE IMAGE ACQUISITION ON A DIGITAL DETECTOR

(75) Inventors: Matthew A. Halsmer, Waukesha, WI (US); Richard J. Warp, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 93 days.

(21) Appl. No.: 10/453,786

(22) Filed: Jun. 3, 2003

(65) Prior Publication Data

US 2004/0247081 A1 Dec. 9, 2004

(51) Int. Cl.$^7$ .................................................. A61B 6/00
(52) U.S. Cl. ...................................... 378/98.12; 378/62
(58) Field of Search ............................. 378/21, 22, 25, 378/26, 62, 95, 98.12, 174, 205; 382/132

(56) References Cited

U.S. PATENT DOCUMENTS

| | | | |
|---|---|---|---|
| 4,613,983 A | 9/1986 | Yedid et al. | |
| 5,048,103 A | 9/1991 | Leclerc et al. | |
| 5,123,056 A | 6/1992 | Wilson | |
| 5,347,570 A | 9/1994 | Haaks | |
| 5,349,625 A | 9/1994 | Born et al. | |
| 5,485,500 A | 1/1996 | Baba et al. | |
| 5,600,701 A | 2/1997 | Baba et al. | |
| 5,610,404 A | 3/1997 | Possin | |
| 5,648,654 A | 7/1997 | Possin | |
| 5,712,890 A | 1/1998 | Spivey et al. | |
| 5,833,607 A | 11/1998 | Chou et al. | |
| 5,844,242 A | 12/1998 | Jalink, Jr. et al. | |
| 5,986,279 A | 11/1999 | Dewaele | |
| 6,055,295 A | 4/2000 | Murthy et al. | |
| 6,097,833 A | 8/2000 | Lobregt et al. | |
| 6,215,849 B1 | 4/2001 | Lienard et al. | |
| 6,236,708 B1 | 5/2001 | Lin et al. | |
| 6,252,931 B1 | 6/2001 | Aach et al. | |
| 6,273,606 B1 | 8/2001 | Dewaele et al. | |
| 6,282,264 B1 | 8/2001 | Smith et al. | |
| 6,465,861 B1 | 10/2002 | Liu et al. | |
| 6,476,394 B1 * | 11/2002 | Amitani et al. | ............. 250/368 |
| 2002/0081010 A1 | 6/2002 | Chang et al. | |
| 2002/0118793 A1 | 8/2002 | Horbaschek | |
| 2002/0159564 A1 | 10/2002 | Wang et al. | |
| 2003/0031290 A1 | 2/2003 | Sugihara et al. | |
| 2004/0101103 A1 * | 5/2004 | Warp et al. | ............. 378/98.12 |
| 2004/0156476 A1 * | 8/2004 | Halsmer et al. | ............. 378/146 |

FOREIGN PATENT DOCUMENTS

| | | |
|---|---|---|
| EP | 0 919 856 A1 | 6/1999 |
| EP | 1 092 391 A1 | 4/2001 |
| WO | WO 00/36820 A2 | 6/2000 |

OTHER PUBLICATIONS

GE Medical Systems, Education: Digital X-ray, Introduction to Digital X-ray technology, available at http://www.gemedicalsystems.com/rad/xr/education/dig_xray_intro, printed on Nov. 4, 2002, 7 pages.

(Continued)

*Primary Examiner*—Edward J. Glick
*Assistant Examiner*—Chih-Cheng Glen Kao
(74) *Attorney, Agent, or Firm*—Foley & Lardner LLP

(57) ABSTRACT

An x-ray system is controlled to obtain a view of an area of a patient that is larger than a field of view of an x-ray detector. Individual images are obtained of portions of the area of the subject that, when combined, can be used to get a view of the area of the subject. Positions of individual images are determined. The positions are preferably calculated to avoid placing structures that tend to move or that are dose sensitive in an area of overlap of the individual images. Also, the positions are preferably calculated to reduce overall exposure to a subject, especially by reducing unnecessary double exposure.

47 Claims, 8 Drawing Sheets

OTHER PUBLICATIONS

Geijer et al., Digital Radiography of Scoliosis with a Scanning Method: Initial Evaluation, Radiology, Feb. 2001, 11 pages, vol. 218, No. 2, The Radiological Society of North America, Inc. (RSNA), Oak Brook, IL.

Wei et al., A new fully automatic method for CR image composition by white band detection and consistency rechecking, Medical Imaging 2001, Image Processing, Progress in Biomedical Optics and Imaging, Feb. 19–22, 2001, 10 pages, vol. 2, No. 27, SPIE—The International Society for Optical Engineering, Bellingham, Washington.

European Search Report for Application No. EP 04 25 3177, 3 pages.

European Search Report for Application No. EP 04 25 3178, 3 pages.

* cited by examiner

METHODS AND APPARATUS FOR MULTIPLE IMAGE ACQUISITION ON A DIGITAL DETECTOR

BACKGROUND OF THE INVENTION

Image pasting, or the creation of a composite image, is usually accomplished by having a system for acquiring individual images that are used to form a combined image with a total field-of-view (FOV) larger than the FOV of the individual images. In most cases, the FOV of the combined image is also larger than the total usable FOV of the x-ray detector used to collect the images. For applications such as full-spine imaging or long-legs imaging, the total coverage of anatomy (e.g., 60–120 cm) exceeds that of most current detectors and film-screen systems.

The process of image pasting may require taking a series of images, one at a time. During this process, a patient is typically asked to stay as still as possible to avoid inconsistencies between subsequent images. This can be uncomfortable for some patients if the process takes an excessive amount of time. Also, an operator imaging a subject may have only a limited amount of time to image the subject, or, alternatively, may have a large number of subjects that the operator must image. A system that could potentially reduce the amount of time that would be needed to image a subject would be preferable.

In image pasting, multiple images are combined to make one continuous image. The ability to accurately join the multiple images often requires that the area of overlap be correctly identified. The higher the resolution of the images, the more crisp the distinctions between structures become, and the easier it is to identify the correct area of overlap. It would be preferable to have a system that could take high quality images.

Further, the ability to identify the correct area of overlap can often be increased when the areas to be overlapped are substantially the same. This is not always possible, since some objects (such as a patient's diaphragm) may tend to move between images. If one of these objects is in the region of overlap then a pasted image would not appear continuous because the moving object could potentially be captured in two different positions. Also, combining the images could be made more difficult because there would be no uniform region of overlap. An image pasting system that could avoid placing these objects in the region of overlap would be preferable.

Additionally, an image pasting algorithm can be used to automate the joining of images. Since images may overlap in a variety of areas, an algorithm could potentially have to search large portions of an image looking for an appropriate area of overlap. Such a system would likely not work as efficiently as possible. A system that can provide a starting point for an image pasting algorithm to locate the region of overlap is desirable.

Also, some parts of a subject may be more sensitive to x-rays than other parts of the subject. For instance, a patient's heart or gonads may be more sensitive to x-ray radiation than other parts of a patient. This may be even more true when the patient is a developing child. In a baggage/package handling context, camera film in a person's travel bag or package may be more sensitive to x-ray radiation than other contents of the bag/package. While these objects can handle x-ray radiation, it is often better to reduce the amount of radiation to which these areas are exposed. In an image pasting application, it would be preferable to exclude these dose-sensitive areas from the region of overlap (i.e. those areas in a region to be imaged that cover avoidable structures that are more sensitive to X-ray radiation than the other potentially avoidable structures in the region to be imaged).

Even more, when detectors with circular input regions are used, the length of overlap necessary to obtain a sufficient total area of overlap to allow accurate joining is greatly increased as compared to the length required for detectors with substantially rectangular input areas. This extra required length can make it significantly more difficult to avoid placing a structure (such as a dose sensitive-structure) in the area of overlap. Thus, it would be preferable for the x-ray detector to have a substantially rectangular area of overlap.

Also, certain medical uses of x-ray detectors take images that start and/or stop just shy of areas that should not be exposed to x-rays if that area is not to be imaged. For instance, one procedure is aimed at obtaining an image of an area starting just below a patient's head and ending just above the patient's waist, thus, the area to be imaged is bracketed by dose-sensitive organs (the organs of the head, and the gonads). In this case, it would be undesirable to allow x-rays to extend above or below the area to be imaged. Thus, it would be preferable to have an x-ray system that can control an x-ray source such that the x-rays do not extend past the area to be imaged.

The teachings herein below extend to those embodiments which fall within the scope of the appended claims, regardless of whether they accomplish one or more of the above-mentioned needs.

SUMMARY OF THE INVENTION

One embodiment is directed to a method for reducing a subject's exposure to x-rays when obtaining a view of an area of a subject that is longer than a length of a maximum field of view of an x-ray detector by obtaining at least two images. The method comprises determining a length of an area to be imaged, and calculating, based on the length of the area to be imaged, a size, in a direction of movement, of an angle of x-rays used to obtain at least one of the at least two images. The size of the angle of x-rays is calculated to reduce exposure to the subject.

Another embodiment is directed to a system configured to reduce a subject's exposure to x-rays when obtaining a view of an area of a subject that is longer than a length of a maximum field of view of an x-ray detector by obtaining at least two images. The system comprises an x-ray source, a collimator coupled to the x-ray source, and a computational unit. The computational unit is configured to determine a length of an area to be imaged, and calculate, based on the length of the area to be imaged, a size, in a direction of movement, of an angle of x-rays used to obtain at least one of the at least two images. The collimator is adjusted to block x-rays from the x-ray source based on the size of the angle of x-rays calculated by the computational unit, thereby reducing exposure to the subject.

An additional embodiment is directed to a method for obtaining a view of an area of a subject that is larger than a field of view used by an x-ray detector. At least two images which have an area of overlap are collected. The method comprises determining a location of an identified structure, and setting the images in locations that avoid placing the identified structure in the area of overlap of the images. The images should be capable of being used to obtain an image with a field of view larger than that used by the x-ray detector to collect the individual images.

An additional embodiment provides a system configured to obtain a view of an area of a subject that is larger than a field of view used by an x-ray detector. At least two images which have an area of overlap are collected. The system comprises an x-ray source, an x-ray detector, a computational unit, and an x-ray detector position change mechanism. The computational unit is configured to input a location of an identified structure, and determine positions of the images collected by the x-ray detector such that the images are in locations that avoid placing the identified structure in the area of overlap of the images. The x-ray detector position change mechanism is then configured to change a relative position between the subject and the x-ray detector in response to a position change control signal from a position change controller such that the x-ray detector can collect images in the positions determined by the computational unit.

Another embodiment provides a control program configured to facilitate obtaining a view of an area of a subject that is larger than a field of view used by an x-ray detector. At least two images which have an area of overlap are collected. The program comprises a program feature to receive an input of a location of an identified structure, and a program feature to determine positions needed of at least two images collected by the x-ray detector. The positions are determined such that the images are in locations that avoid placing the identified structure in the area of overlap of the images.

Another embodiment is directed to a method for obtaining a view of an area of a patient that is larger than a field of view used by an x-ray detector by obtaining at least two images, the images having an area of overlap. The method comprises determining a location of an organ, and setting the images in locations that avoid placing the organ in the area of overlap of the images. The images should be capable of being used to obtain an image with a field of view larger than that used by the x-ray detector which was used to collect the images.

An additional embodiment is directed to a method for controlling an x-ray system for obtaining a view of an area of a subject that is larger than a field of view of an x-ray detector by obtaining individual images of portions of the area of the subject that, when combined, can be used to get a view of the area of the subject. The method comprises calculating positions of the x-ray detector necessary to obtain the individual images, holding a relative location between the subject and an x-ray source constant while the images are being collected, and controlling the position of the x-ray detector with a control signal to collect the images based on the calculated positions.

An additional embodiment provides a method for controlling an x-ray system for obtaining a view of an area of a subject that is larger than a field of view of an x-ray detector by collecting individual images of portions of the area of the subject that, when combined, can be used to get a view of the area (typically the entire area) of the subject. The method comprises calculating positions of the x-ray detector necessary to collect the individual images, the positions of the x-ray detector being a non-uniform length apart. The method also comprises controlling movement of the x-ray detector with a control signal to move the x-ray detector to the calculated positions.

Another embodiment provides a method for determining a minimum number of x-ray images needed to image a subject in an x-ray system where an angle of x-rays that is used is held constant once the image collection process begins. Further, the method applies to a system where a relative position between the subject and an x-ray source is held constant, and where a length of an area of the subject to be imaged is longer than a length of a field of view of an x-ray detector. The method comprises determining a total length to be imaged, determining a maximum angle of x-rays that can be used to image the area of the subject using an x-ray detector, determining an amount of overlap, and calculating the minimum number of images needed based on the length to be imaged, the maximum angle of x-rays, and the amount of overlap.

Another embodiment is directed to a method for controlling an x-ray system for obtaining a view of an area of a subject that is larger than a field of view of an x-ray detector by obtaining individual images of portions of the area of the subject that, when combined, can be used to get a view of the area of the subject. The method comprises receiving a user input indicative of a desired starting position, receiving a user input indicative of a desired ending position, and controlling operation of the x-ray system in obtaining the individual images based on the starting position and the ending position.

DETAILED DESCRIPTION OF THE PREFERRED EMBODIMENTS

Figure 1:
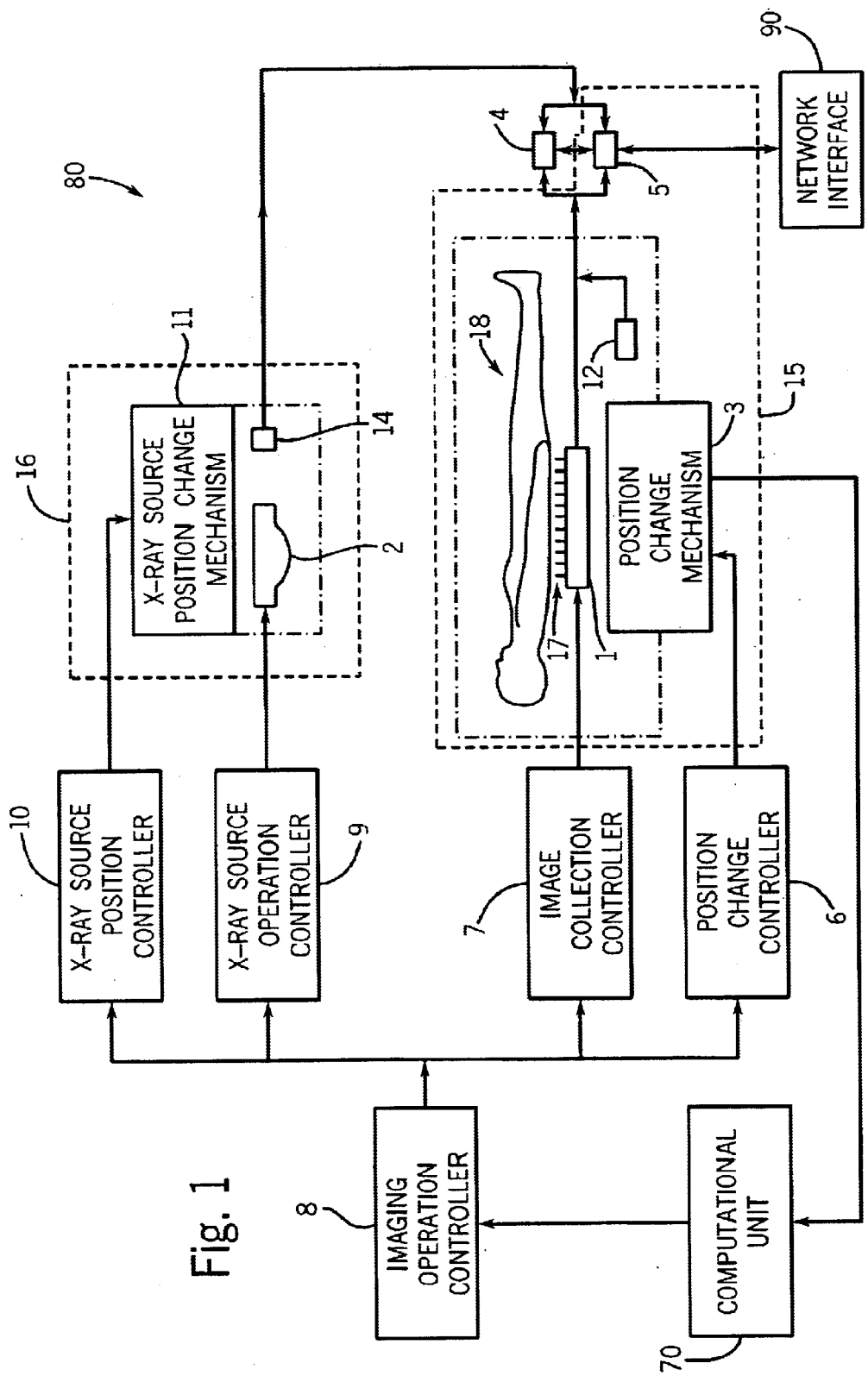
FIG. 1 is a schematic diagram of an x-ray system according to one embodiment of the invention.

Referring to FIG. 1, an x-ray system 80 includes an x-ray source 2 that generates x-rays and an x-ray detector 1 that collects images of a subject based on the generated x-rays. X-ray detector 1 can include an x-ray grid 17 to block some of the scattered x-rays. Operation of x-ray detector 1 can be controlled by an image collection controller 7. A relative position between X-ray detector 1 and subject 18 is changed by a detector position change mechanism 3. Detector position change mechanism 3 is controlled by a position change controller 6. Detector position change mechanism 3 could move the detector, the subject, or some object that would facilitate a change in the relative position between subject 18 and x-ray detector 1.

X-ray source 2 typically includes a high voltage generator and an x-ray tube. X-ray source 2 can also include an adjustable collimator. Operation of x-ray source 2 can be controlled by an x-ray source controller 9. X-rays from X-ray source 2 have their position changed by an x-ray source position change actuator 11. X-ray source position change actuator 11 can be the same mechanism as detector position change mechanism 3 (such as when using a C-arm gantry), or can be a separate mechanism. X-ray source position change actuator 11 may be controlled by an x-ray source position controller 10.

X-ray system 80 can also include an imaging operation controller 8 that controls the various functions of the system. Also, X-ray system 80 typically includes a processor 4 for processing and/or joining images collected by X-ray detector 1. X-ray system 80 can also include an image storage enabling unit 5 that enables storage of images collected by X-ray detector 1, and a positioner 12 and an inclinometer 14 for obtaining geometry information of images collected by x-ray detector 1.

X-ray system 80 can further include a computational unit 70, that can be used to compute various factors associated with the image pasting operation, including the positions of x-ray detector 1 and the angle of x-rays that is used to collect an image.

Figure 2:
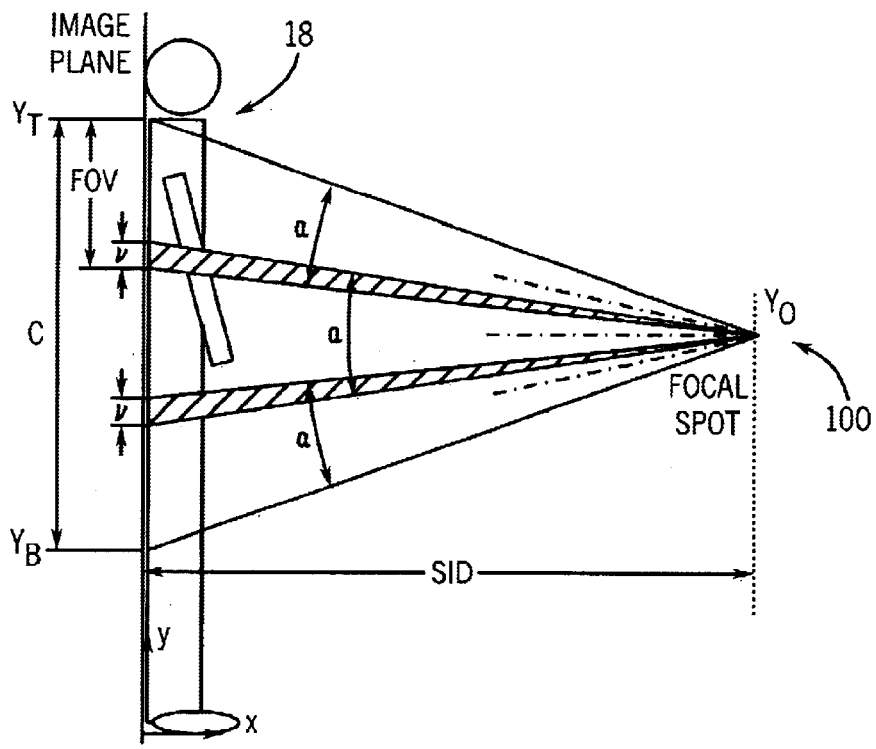
FIGS. 2 and 3 are diagrams of an image acquisition system according to another aspect of the invention.
Figure 3:
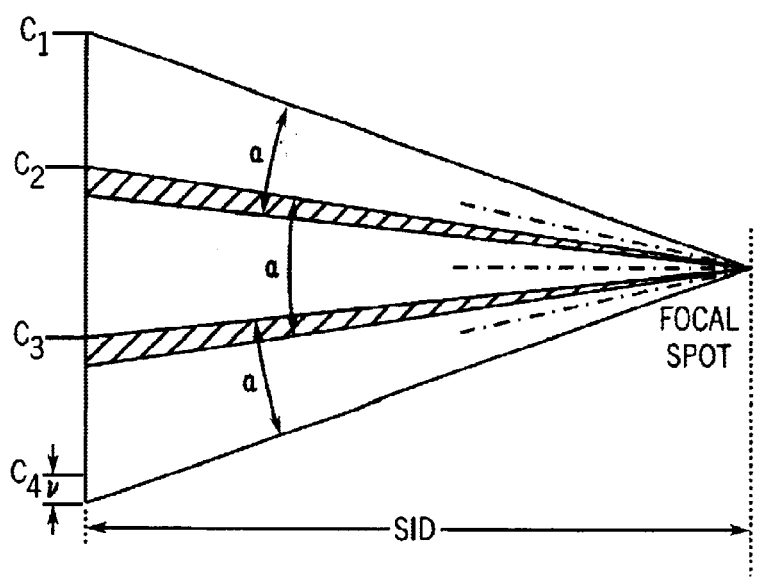

Referring to FIGS. 2 and 3, an exemplary embodiment of a system for computing locations of images includes an x-ray source 2 that angulates across focal point 100. X-ray source 2 uses a constant angle of x-rays "α" for each image. Each image pair has a constant amount of overlap "v" as x-ray detector 1 moves along the y-axis just behind subject 18.

An operator can enter a top ($y_t$) position and a bottom ($y_b$) position which determines the final image length (c). The top and bottom positions can be entered based on user inputs such as moving a detector to a top and bottom position; using a beam of light emitted from the x-ray source which is then used to illuminate the top and bottom positions; placing a signal transmitter at the top and/or bottom position; placing the detector at the top position and placing another device at the bottom position; placing the detector at a recognizable position (such as the belly button, feet, waist, shoulders, etc), entering a subject's characteristics (tall/short, exact height, inseam and other component information, etc.), and entering the type of procedure; and/or some other method of inputting the top and bottom positions. If data is entered, it can be entered manually or can be based on a subject's file, which file may be accessed over a network.

A user can also enter the image plane to source distance (SID), maximum FOV, and desired overlap (v). Alternatively, these parameters can be predefined or can be computed based on additional data. Some of the variables to be determined from the user inputs are the number of images taken (N), the angle of collimation ($\alpha_i$), the actual field of view ($FOV_i$), the center ray angles at exposure ($\phi_i$), the focal spot exposure height ($y_0$), and the exposure positions of the detector ($y_i$).

The focal spot exposure height $y_0$ will be defined as halfway between the top and bottom position.

$$y_o = \frac{c}{2} + y_b \qquad (1)$$

The next step is to decide which collimation strategy should be implemented. If the collimator is allowed to change dynamically between exposures, then the FOV could be equivalent for each exposure, a strategy to avoid naturally moving anatomy could be used, or some other strategy could be used.

When a collimator position is held constant between images, in order to find the minimum number of exposures to be taken, a few intermediate parameters may be defined.

The overall exposure angle θ is found with equation 2.

$$\theta = 2 * \tan^{-1}\left(\frac{c/2}{SID}\right) \qquad (2)$$

The maximum collimated angle $\alpha_{max}$ is generally defined from the maximum imaging size of the detector that will be used $FOV_{max}$ when at the extreme end of the coverage area as set forth in equation 3. This number represents the maximum angle of x-rays that can be used at the extreme end without exposing subject 18 to x-rays that can not be used by x-ray detector 1 to create an image.

$$\alpha_{max} = \tan^{-1}\left(\frac{c/2}{SID}\right) - \tan^{-1}\left(\frac{c/2 - FOV_{max}}{SID}\right) \qquad (3)$$

The smallest overlap angle $v_{\_max}$ of all of the overlap angles would be the angle that covers the overlap distance 'v' at the extreme overlap segment. This is found in equation 4 below.

$$\gamma_{v\_max} = \tan^{-1}\left(\frac{c/2 - FOV_{max} + v}{SID}\right) - \tan^{-1}\left(\frac{c/2 - FOV_{max}}{SID}\right) \qquad (4)$$

These three angular parameters ($\theta$, $\alpha_{max}$, $\gamma_{v\_max}$) can be used to estimate the minimum number of images that need to be taken in order to cover the entire region of interest while maintaining the minimum amount of overlap. The relationship between these three angular parameters is shown in equation 5.1 below. Upon rearranging for N, the number of images can be found from equation 5.2.

$$\theta = N * \alpha_{max} - (N-1) * \gamma_{v\_max} \qquad (5.1)$$

$$N = \text{smallest integer not less than } \left(\frac{\theta - \gamma_{v\_max}}{\alpha_{max} - \gamma_{v\_max}}\right) \qquad (5.2)$$

Using this approach, the minimum number of images N can be found for a single collimator setting that will maximize the detector size.

Now that the minimum number of exposures has been determined the actual collimation angle α can be found. Looking at FIG. 3, a new parameter, $c_i$, is introduced, which corresponds to the position of the top of exposure area for a given image 'i'.

So the top of exposure one $c_1$ should be at the top of the defined space, and then the top of the second exposure $C_2$ is the angulated distance down $\alpha_{FOV}$, plus the overlap height v, and so on all the way down the exposure area.

$$c_1 = \frac{c}{2} \qquad (6.1)$$

$$c_2 = SID * \tan\left[\tan^{-1}\left(\frac{c_1}{SID}\right) - \alpha_{FOV}\right] + v \qquad (6.2)$$

$$c_3 = SID * \tan\left[\tan^{-1}\left(\frac{c_2}{SID}\right) - \alpha_{FOV}\right] + v \qquad (6.3)$$

$$c_4 = SID * \tan\left[\tan^{-1}\left(\frac{c_3}{SID}\right) - \alpha_{FOV}\right] + v \qquad (6.4)$$

$$c_{N+1} = SID * \tan\left[\tan^{-1}\left(\frac{c_N}{SID}\right) - \alpha_{FOV}\right] + v \qquad (6.5)$$

Ideally, the value for $C_{N+1}$ would perfectly match the bottom of the desired exposure region not including the overlap, so the amount of error E would be:

$$E = -\left(\frac{c}{2}\right) - (c_{N+1} - v) \quad (7)$$

To find the desired collimation angle, the angulated distance $\alpha_{FOV}$ is varied until the error E is about zero.

Once the final collimation angle is found, equations 6.1–6.5 will be used again to find the final position for the top of each individual image. It should be recognized that for some images, the input FOV of x-ray detector 1 will be larger than the size of the image. In these cases, the top of x-ray detector 1 need not coincide with the top of the image so long as the image can be collected by using x-ray detector 1.

Using the value of the top location of each image, equation 8 can be used to find the desired angle for the tube angulation assembly.

$$\phi_i = \tan^{-1}\left(\frac{c_i}{SID}\right) - \frac{\alpha_{FOV}}{2} \quad \text{(for } i = 1 \text{ to } N\text{)} \quad (8)$$

Instead of using equations 5.1 and 5.2 to estimate the number of images (N) that are needed, the number of images can also be calculated using the equations below.

$$C_1 = \frac{c}{2} \quad (5.3)$$

$$C_2 = SID * \tan\left[\tan^{-1}\left(\frac{c_1}{SID}\right) - \alpha_{max}\right] + v \quad (5.4)$$

$$C_3 = SID * \tan\left[\tan^{-1}\left(\frac{c_2}{SID}\right) - \alpha_{max}\right] + v \quad (5.5)$$

$$C_4 = SID * \tan\left[\tan^{-1}\left(\frac{c_3}{SID}\right) - \alpha_{max}\right] + v \quad (5.6)$$

$$\vdots$$

$$C_{N+1} = SID * \tan\left[\tan^{-1}\left(\frac{c_N}{SID}\right) - \alpha_{max}\right] + v \quad (5.7)$$

This is continued until $C_{N+1} - V$ is less than or equal to $$-\frac{c}{2}$$

(alternately, until $$C_{N+1} - V + \frac{c}{2}$$

is less than or equal to 0). The minimum number of images required would be $C_N$. Also, the difference between $$C_{N+1} - v \text{ and } -\frac{c}{2}$$

can be used to estimate $\alpha_{FOV}$.

Figure 4:
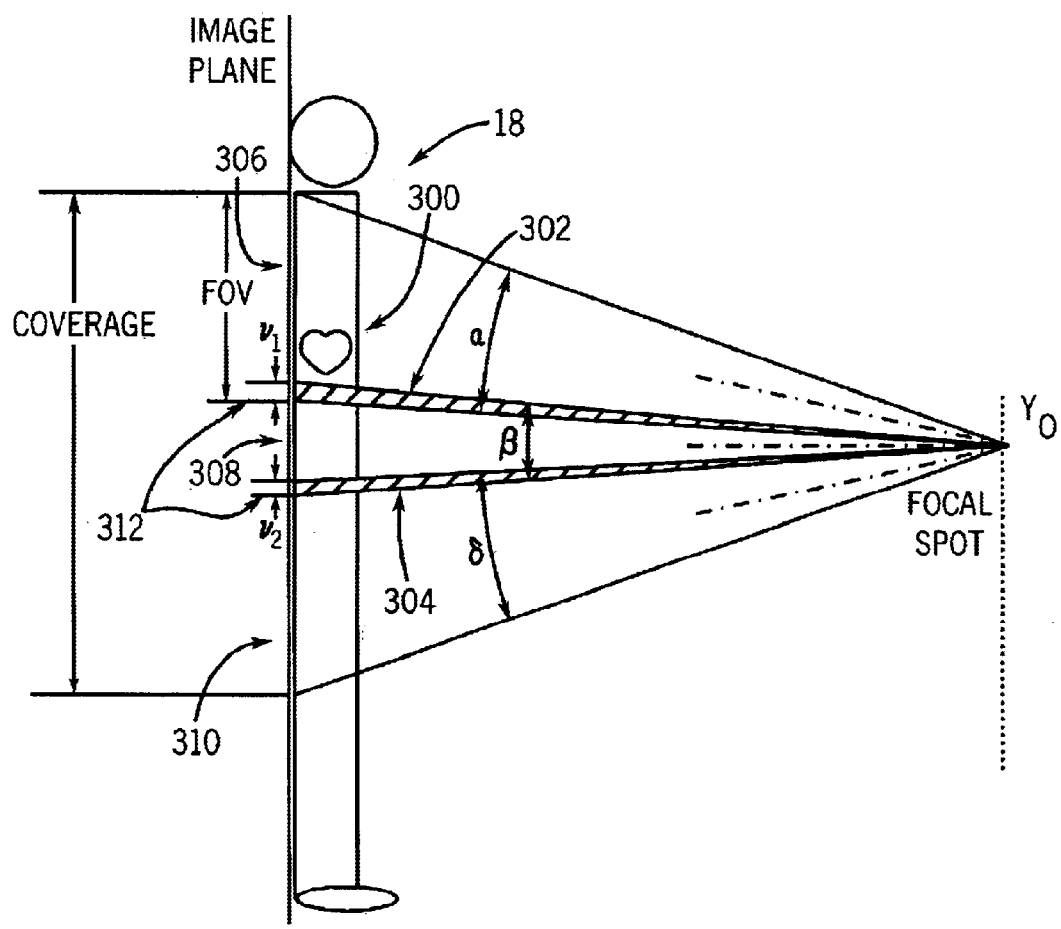
FIG. 4 is a diagram of an image acquisition system according to another aspect of the invention.

Referring now to FIG. 4, an algorithm can also be used to avoid placing identified structures 300 (such as those that are dose sensitive or those that tend to move) in the regions of overlap 302 or 304. Avoiding placing an identified structure 300 in an area of overlap may involve using non-uniform collimator angles ($\alpha$, $\beta$, and $\delta$). Also, avoiding placing an identified structure 300 in an area of overlap may involve varying an amount of overlap 312 between pairs of images (306 and 308, 308 and 310). Identifying the locations of identified structures 300 can be accomplished in manners similar to those discussed in relation to FIGS. 2 and 3 for determining the top point ($y_t$) and bottom point ($y_b$). Some structures, such as a patient's skin, will likely exist throughout the entire region to be imaged, and will thus not be avoidable.

Computational unit 70 can use the inputs to determine the detector positions, collimator angles, and overlap regions necessary to obtain a set of images (306, 308, 310) that are pastable and that avoid placing critical region 300 in an area of overlap. This data can be used by imaging operation controller 8 to control the operation of x-ray system 80.

Figure 5:
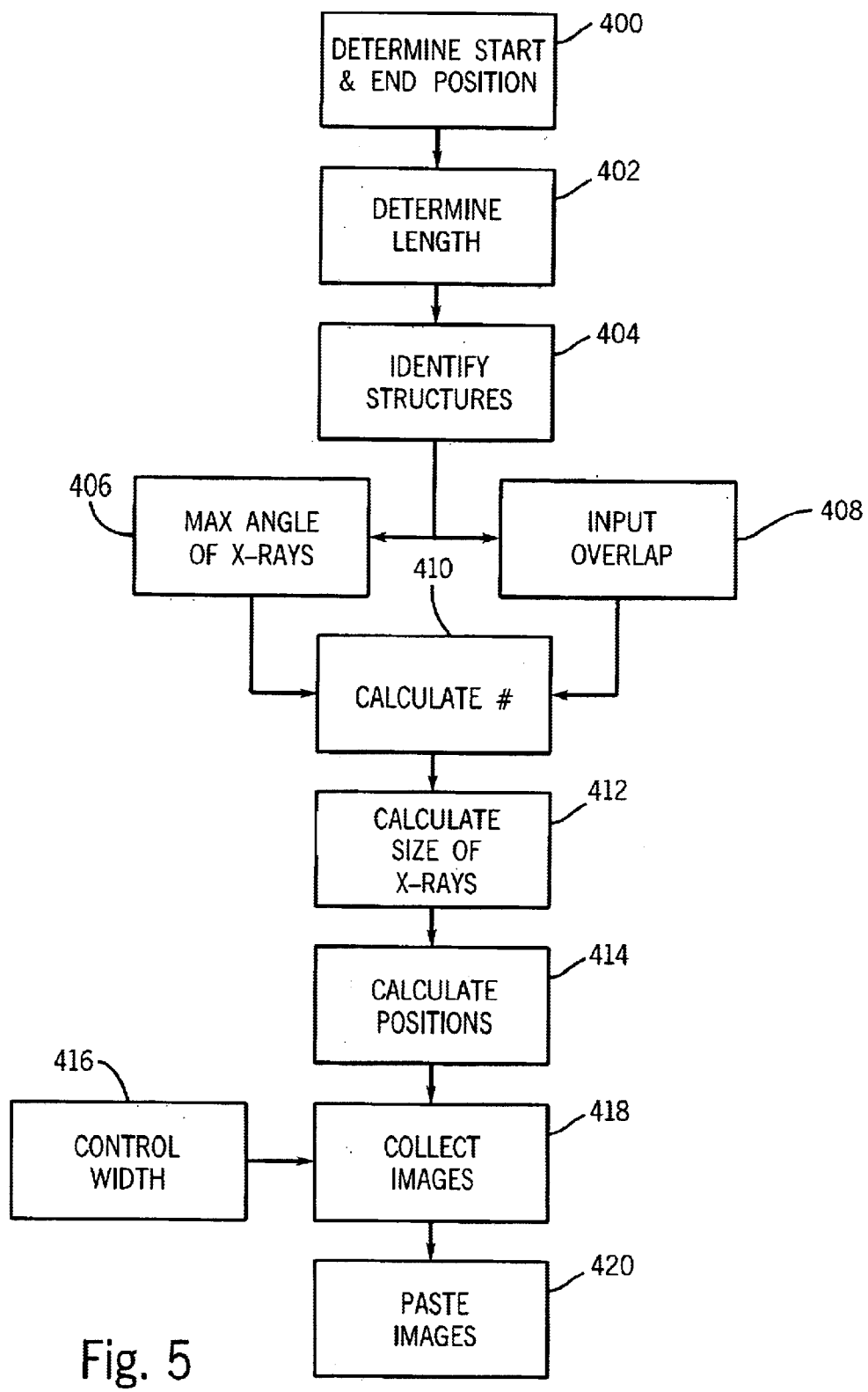
FIG. 5 is a flow diagram according to another embodiment of the invention.

Referring to FIG. 5, a method of collecting images with an image pasting x-ray system includes determining starting and ending positions for the area to be imaged at block 400. The starting and ending positions can be manually input by a user. For instance, a user could enter starting and ending heights (or distances) into a computer, a user could set the detector at both the starting and ending positions, etc. The starting and ending positions could also be achieved automatically. For instance, a camera could take a digital photograph of a subject, which photograph could be used, based on the type of procedure, to determine the starting and ending positions. Further, the subjects characteristics could be imported from a file, and the file could be used to determine the starting and ending positions of the procedure. Further still, the x-ray detector could run a quick pre-scan and use the pre-scan to determine the starting and ending positions. Also, the starting and ending positions could be a combination of manual input (such as a known location on the subject or other reference position) and automatic determination.

Once the starting and ending positions have been determined at block 400, the length of the area to be imaged is determined at block 402. Length may be determined by storing the starting and ending points, by converting the starting and ending points into a distance, by converting the starting and ending points into an angular length (potentially based on the SID), or by some other method.

Next, a determination is made at block 404 as to whether a structure 300 has been identified as not belonging in an area of overlap, the maximum angle of x-rays is calculated at block 406, and an input of the desired amount of overlap is received at block 408. The input could be received from a user. The input could also be received from other program logic based on the type of procedure, the characteristics of a subject, the degree of certainty desired relating to the accuracy of the overlap, the requirements of an image pasting algorithm used to paste the individual images, etc. The amount of overlap could also be a set, assumed, or calculated amount. The amount of overlap could be any number from zero to up to just shy of a length, in the direction of movement, of the field of view of the detector that is used to obtain the desired images. Preferably, the overlap is at least 5% of the length of the field of view of the detector in the direction of movement, but not more than 25% of the length of the field of view of the detector. More preferably, the overlap is between about 10% to 20% of the length of the field of view of the detector. Most preferably, the overlap would not be more than 12.5% of the length of the field of view of the detector.

Once the length, the identified structures 300, the maximum angle of x-rays, and the desired overlap are inputted, the minimum number of images needed to gain images of the entire area is calculated at block 410. The calculation at block 410 is preferably made for a system that uses an x-ray source 2 which has its location fixed with respect to the subject. Further, x-ray source 2, or some device associated with x-ray source 2, preferably causes the x-rays to angulate between subsequent images. Further still, the calculation can be made where the angle of x-rays (α) is held constant for each image.

Once the number of x-rays has been calculated at block 410, the size of the angle of x-rays can be calculated at block 412, and the relative positions of the detector with respect to the subject can be calculated at block 414.

Once the size of the angle of x-rays and the relative positions of the detector have been calculated, the images can be collected at block 418. Further, the width of the x-rays can be adjusted at 416. A user may narrow the width of the angle of x-rays to hone in on the area of interest, to reduce the exposure of the subject to x-rays, and/or to reduce the amount of potential scattering of x-rays.

Once the images have been collected, the images can be pasted at block 420. The pasted image and the individual images can be transferred and/or accessed using a network interface 90. Further, a billing record can be generated based on the use of x-ray system 80 and then be transferred across the network.

The process of computing the minimum number of images to be taken and controlling the images can sometimes be used to decrease the total amount of x-rays to which a subject is exposed. For instance, it can be used to decrease the amount of unnecessary double exposure in a procedure by reducing the unnecessary overlap.

Also, controlling the positioning of a detector and/or controlling collection of images with a control program can allow for more accurate positioning and a more consistent amount of overlap which could lead to a more accurate, faster image pasting process.

Figure 6A:
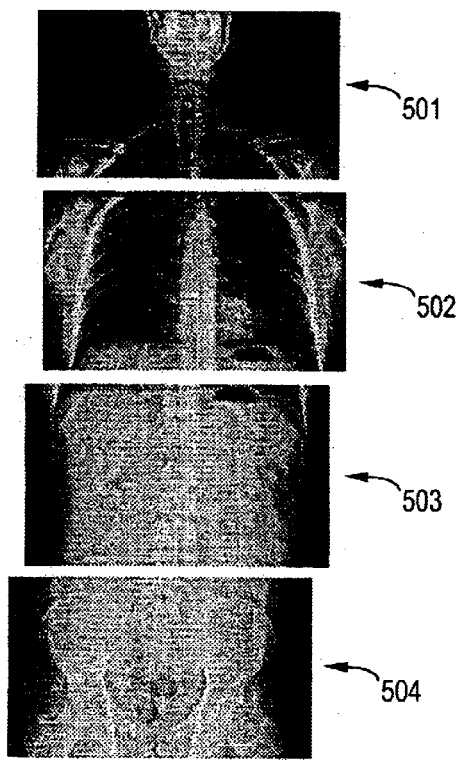
FIGS. 6a and 6b are images taken using a system according to one aspect of the invention.
Figure 6B:
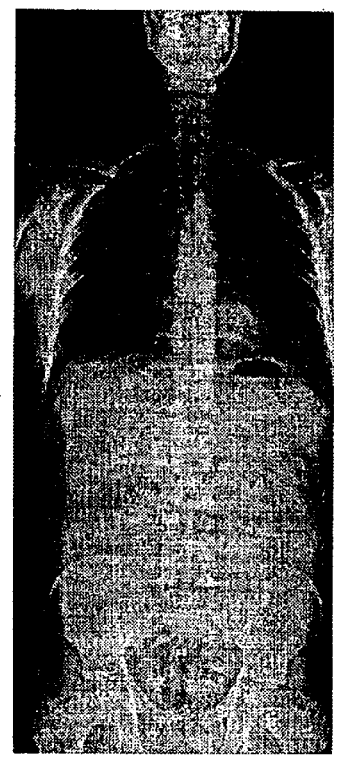

Referring to FIGS. 6a and 6b four individual images 501, 502, 503, 504 have been collected with a flat-panel x-ray detector at four different relative positions which had been calculated according to the exemplary embodiment described with respect to FIGS. 2 and 3. The individual images 501, 502, 503, 504 can be joined to form a single pasted image 505.

Figure 7:
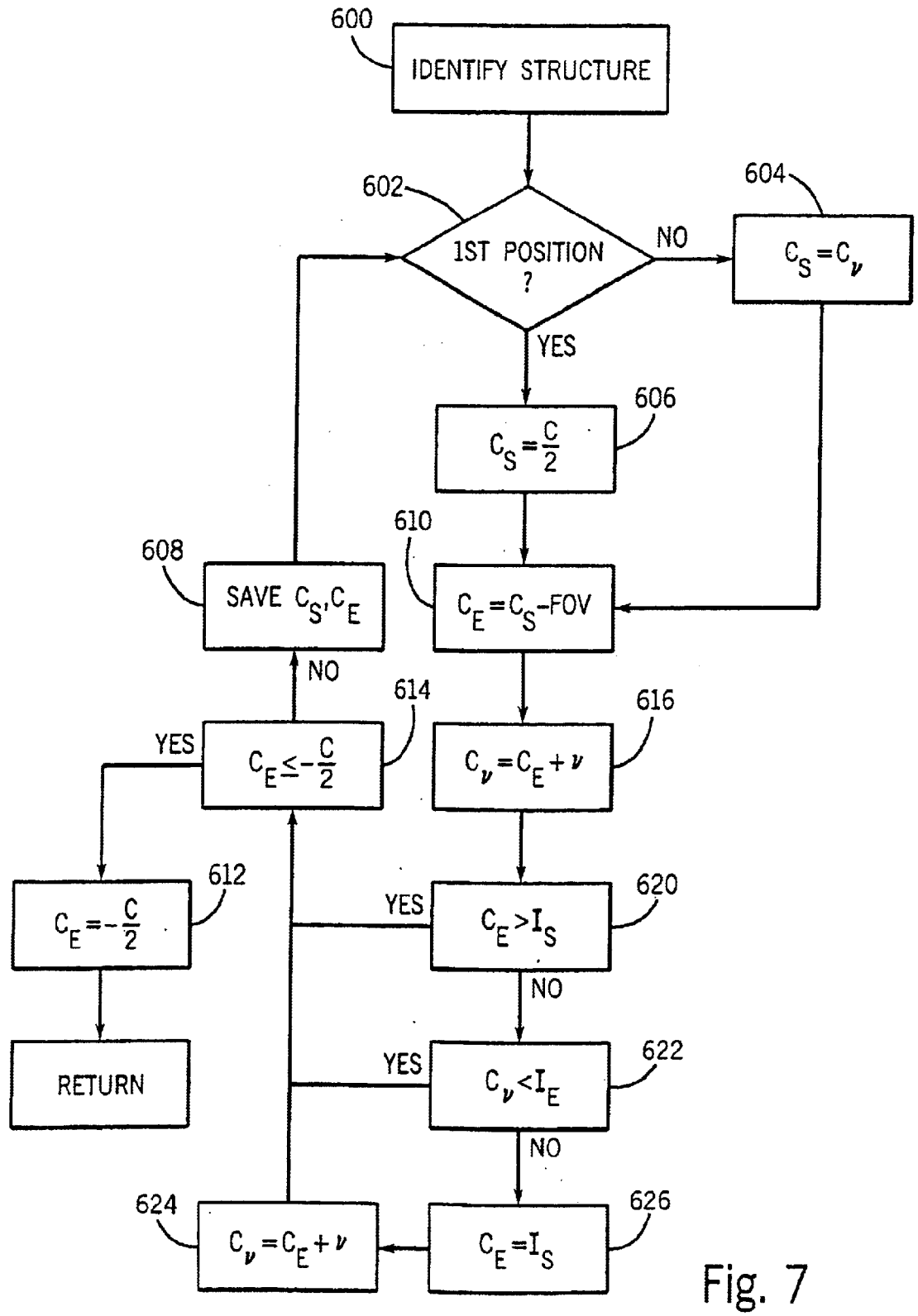
FIG. 7 is a flow diagram according to another embodiment of the invention.

Referring to FIG. 7, a method of obtaining collected images where an identified structure 300 is not in a region of overlap includes determining the location of an identified structure, such as an organ, at block 600. The location of identified structure 300 can be entered in a number of manners. For instance, a user could manually input the location by keying in the location, by holding the detector (or a portion of the detector) over the area, by using a radio frequency tag whose position is identified, by any of the means listed for entering a starting and ending position, and/or any other means of inputting. Alternatively, a location of identified structure 300 may be estimated based on various criteria. For instance, if a person is standing in front of the detector (or has a body part in a known location), a person's physical characteristics (height, weight, inseam, etc.) can be used to estimate the location of identified structure 300. Additionally, the location of identified structure 300 can be based on the type of procedure. For instance, in a head to hip procedure, with a given starting and/or ending point, a location of a patient's heart and diaphragm can be estimated. In addition, these techniques may be combined. For instance, given a user input of the location of the gonads, the location of the heart and diaphragm can be estimated based on a patient's other characteristics (such as a person's height, weight, etc.).

Next, it is determined whether a first position is being recorded at block 602. If a first position is being recorded, the image starting position ($C_S$) of the individual image is set equal to the starting position $$\left(\frac{c}{2}\right)$$

of the area to be imaged at block 606. If a first position is not being recorded at block 602, the starting position is set equal to the start of the overlap region ($C_v$) of the previous individual image at block 604. The ending position of the image ($C_E$) is set equal to the starting position minus the field of view of x-ray detector 1 in the direction of measurement at block 610. If only a portion of the detector will be used, the field of view of that portion of the detector can be used instead. $C_v$ is then set equal to the ending position plus the desired overlap distance (v) at block 616.

Next it is determined at block 620 whether $C_E$ is less than the top point ($I_S$) of identified structure 300. If it is not, then it is determined at block 622 whether the $C_v$ is less than the bottom point ($I_E$) of identified structure 300. If it is not, then $C_E$ is set equal to $I_S$ at block 626. This allows the bottom point of the image to be at a position just above identified structure 300, which would mean that the region of overlap would be just above identified structure 300. A cushion could also be built into the system such that the region of overlap would be a certain distance from identified structure 300. Once $C_E$ is established at block 626, a new $C_v$ is calculated at block 624. The amount of overlap (v) could be a different amount (such as a smaller amount) for block 624 than for block 616. When $C_v$ is calculated at block 624 and when the answer is yes in blocks 620 or 622 a determination is made at block 614 as to whether $C_E$ is at or past the end point of the area to be imaged. If it is, then $C_E$ is set equal to the end point at block 612. If $C_E$ is not at or past the end point, then the starting and ending point of the image are saved at block 608, and positions for a new individual image are calculated by going back to block 602.

When all of the values for the various images have been calculated, the angle of x-rays for each image can be calculated. If a stepping motion is used for x-ray source 2, the angle would be $2*\tan^{-1}((C_S-C_E)/(2*SID))$ for each image. If an angulation motion is used for x-ray source 2, positions can be calculated by applying $C_S$ and $C_E$ to the equations previously listed above, and the angle of x-rays used would be equal to the difference in the angle of $\Phi$-$C_S$ and $\Phi C_E$.

More complicated methods can be used to judge whether two regions of overlap ($C_v$, $C_E$) and ($C_v'$, $C_E'$) overlap, and can adjust the positions of the images to avoid such overlap. For instance, two regions of overlap would be present when $C_v'$ is greater than $C_S'$. A system could then readjust $C_E$ and $C_v$ such that $C_S'$ (which is based on $C_v$) would no longer be less than $C_v'$. Alternatively, a smaller amount of overlap (v) could be used for those images.

Additionally, more than one identified structure 300 can be taken into account. For instance, a technician imaging a patient may want to avoid placing each of the heart, the diaphragm, and the gonads in regions of overlap.

Also, the overlap amount (v) need not be a preset number. It could be calculated based on a variety of factors, including the type of procedure, characteristics of the individual, the size ($C_S$, $C_E$) of an image, etc.

These procedures can all be carried out by logic/software in computational unit 70.

A device for inputting various data to computational unit 70 could include a light source that shines on the subject. The device could also include adjustable panels that can be used to block light from the light source. An operator can operate the adjustable panels such that light is allowed to shine on the non-identified areas 300' of the subject, but light does not shine on the identified areas containing identified structures 300. The input devices determine which panels are open. Based on information transmitted from the input devices, the distance to the subject, and/or the angle of the light source, computational unit 70 can identify regions to avoid placing in an area of overlap—thus avoiding placing an identified structure 300 in an area of overlap. The panels can also be used to identify the starting and ending position of an image to be acquired.

Referring again to FIG. 1, x-ray device 1 images a subject of interest 18. Subject of interest 18 can be any number of subjects where taking an x-ray image of the subject is desired. Some typical subjects of interest are human patients to make diagnosis, sealed packages to determine contents, and welding joints to ensure a complete weld.

If subject of interest 18 is a human patient, the patient can stand in any position, e.g., posterior-anterior (PA), anterior-posterior (AP), lateral (LAT), etc. The patient can also be in a dorsal or ventral position on a platform, or any other desired position.

Imaging operation controller 8 controls x-ray detector 1 to collect at least two images at two separate positions. Specifically, imaging operation controller 8 controls x-ray source operation controller 9 and image collection controller 7 to gather images. Imaging operation controller 8 further controls position change controller 6 to control a change in the relative position between x-ray detector 1 and subject of interest 18, so that x-ray detector 1 and subject of interest 18 are placed in at least two different relative positions. As mentioned previously, these positions can be controlled based on the results of computational unit 70.

X-ray source operation controller 9 controls x-ray source 2 to generate x-rays. X-ray source operation controller 9 can also control x-ray source 2 to change the collimator angle. X-rays are typically generated by having a high voltage generator generate a high voltage signal which causes an x-ray tube to emit x-rays.

X-rays pass through the subject of interest 18 and can be detected by x-ray detector 1. Image collection controller 7 controls to collection of images at at least a first and a second position. Image collection controller 7 may operate by controlling x-ray detector 1 to detect x-rays. Alternatively, x-ray detector 1 may constantly be detecting images and image collection controller 7 may control the collection of only a particular image that has been detected. Image collection controller 7 may operate in many ways so long as the image collection controller 7 controls the system to collect an image at at least a first and a second position.

An image collected by x-ray detector 1 may then be sent to image storage enabling unit 5 which enables the storage of the image detected by x-ray detector 1. The image collected by x-ray detector 1 may alternatively be sent to the processor 4 to undergo pre-processing operations. The pre-processed image may then be sent to the image storage enabling unit 5, or may be further processed.

A positioner 12 can be used to measure the geometry associated with the image by measuring the geometry of the detector. Also, an inclinometer 14 can be used to measure the geometry associated with the image by measuring the angle of the x-ray tube. The geometry measurement devices (such as a positioner or an inclinometer) send the information to either the processor 4 or the storage enabling unit 5. The geometry measurement devices may send information relating to the geometry of the image along with the image, or as a separate signal or signals.

Optionally, x-ray source position controller 10 may control x-ray source position change actuator 11 to move x-ray source 2 from one position to another position. Changing the position of x-ray source 2 could include changing the location of x-ray source 2, could include changing the angle of x-ray source 2, could involve some combination of both movements, or could occur in some other manner. If x-ray source 2 changes position, it may change before, after, or at the same time as the relative position between x-ray detector 1 and subject of interest 18 changes.

Also, the various controllers may be separate controllers, or all part of one or more control signals. For instance, in response to a single control signal, position change mechanism 3 may change the relative position between x-ray detector 1 and subject of interest 18, and in response to the same control signal, an image may be collected. Specifically, the presence of the control signal may prompt movement, and the termination of the control signal may indicate that an image should be collected. The various controllers involved in the system may be combined in any number of ways. Reference to the controllers individually or as a first controller, a second controller, . . . $n^{th}$ controller is not meant as an indication that the controllers are physically separate and distinct.

After the subsequent relative position between subject of interest 18 and x-ray detector 1 has been set, a subsequent image is taken in the same-manner as the original image. The subsequent image may be sent to the image storage enabling unit 5, or may be sent to the processor 4 in the same manner as the original image.

Geometry measurement devices 12 and 14 may also measure the geometry associated with the second image and send that information to either processor 4 or storage enabling unit 5. Geometry measurement devices 12 and 14 may send information on the geometry of the image along with the image, or as a separate signal.

More images may then be detected by repeating the operations listed above. When all the images are taken, the plurality of images may then be joined to form a pasted image.

X-ray detection unit 15 (including the x-ray detector 1, the x-ray position changing mechanism 3, and the storage enabling unit 5) and x-ray generating unit 16 (including the x-ray source 2 and the x-ray source position change actuator 11) can be manufactured and sold as two separate units. The two separate units can then be controlled to operate together by imaging operation controller 8 (which can be part of a separate control unit, a part of x-ray generating unit 16, or a part of x-ray detection unit 15), after the individual units have been installed.

Figure 8:
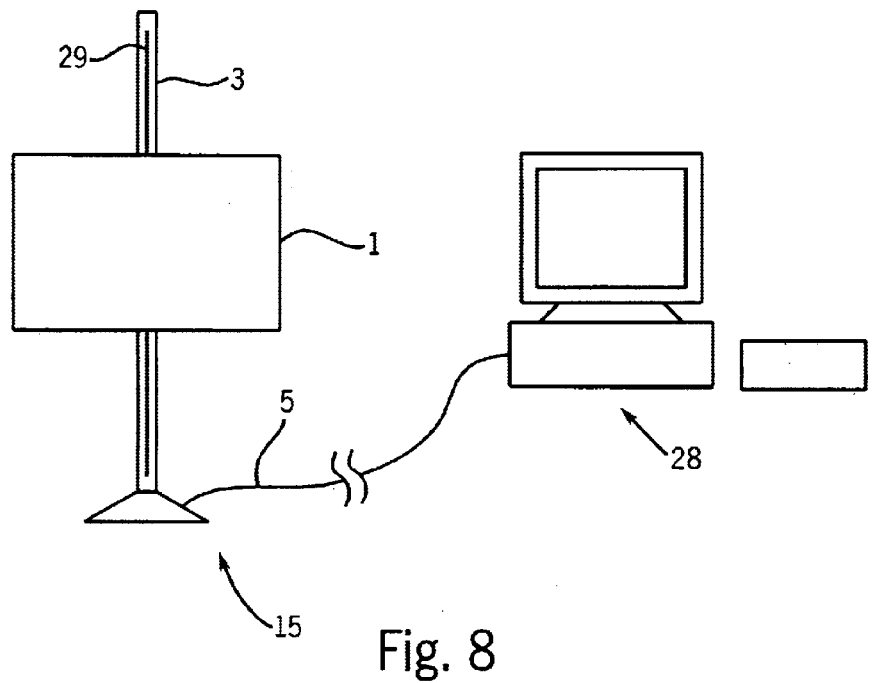
FIG. 8 is a schematic diagram of an x-ray system according to another embodiment of the invention.

Referring to FIG. 8, an x-ray detection unit 15 according to one embodiment of the present invention includes an x-ray detector 1, a position changing mechanism 3, and a storage enabling unit 5. The x-ray detector 1 is a flat panel x-ray detector with a rectangular field of view. Position changing mechanism 3 includes a motor which moves x-ray detector 1 along a track 29. Storage enabling unit is a data port connection which allows a collected image to be stored in computer 28. Position change mechanism 3 is responsive to a position change control signal received from computer 28. X-ray detector 1 may be responsive to an image collection control signal from computer 28 to collect images, or computer 28 may sort through the images detected by x-ray detector 1 to determine which ones should be collected in response to an image collection control signal generated within software of computer 28.

X-ray detector 1 is preferably a flat-panel detector. X-ray detector 1 includes an x-ray grid 17. X-ray grid 17 can either be integrated into x-ray detector 1, or sold as a removable unit. X-ray grid 17 tends to remove noise from the detected image by shielding x-ray detector 1 from some of the x-rays that have been scattered.

Position change mechanism 3 can be any number of mechanisms which are capable of changing the relative position between x-ray detector 1 and subject of interest 18. Preferably, position change mechanism 3 includes a motor which moves x-ray detector 1 in a linear motion along a vertical track. Position change mechanism 3 could also be any number of other mechanisms such as a motor which moves a platform on which subject of interest 18 is located, a hydraulic lift, etc.

Images that have been collected may be sent to a storage enabling unit 5. Storage enabling unit 5 could be a temporary or permanent memory source integrated within the device, a removable memory source, a drive/removable medium system, a data port, or some other device that enables storage of the collected images.

Processor 4 may perform pre-processing operations on the individual images such as correcting image fall-off or enabling intensity normalization. This allows images to appear more even and makes for smoother transitions. Processing may also be done on the image after it has been pasted together. Some examples of such post-processing techniques include adjusting the contrast and making transitions between individual images in the pasted image appear smoother. Other examples of post-processing methods that can be used include histogram equilization and dynamic range reduction.

Processor 4 may also contain software that joins the collected images. The software that joins the images together can use information from computational unit 70 to aid in the joining process. For instance, information relating to the amount of overlap between images could be used to provide a starting point and/or increase the efficiency with which images are joined.

The pasted image can be displayed to the user. The display can also contain the original images, especially with softcopy display.

The pre-processing, joining, and post-processing operations can be performed by one or more processors. It should also be noted that the processing steps can be performed by one or more separate and distinct devices which handle the images collected by x-ray system 80.

Figure 9A:
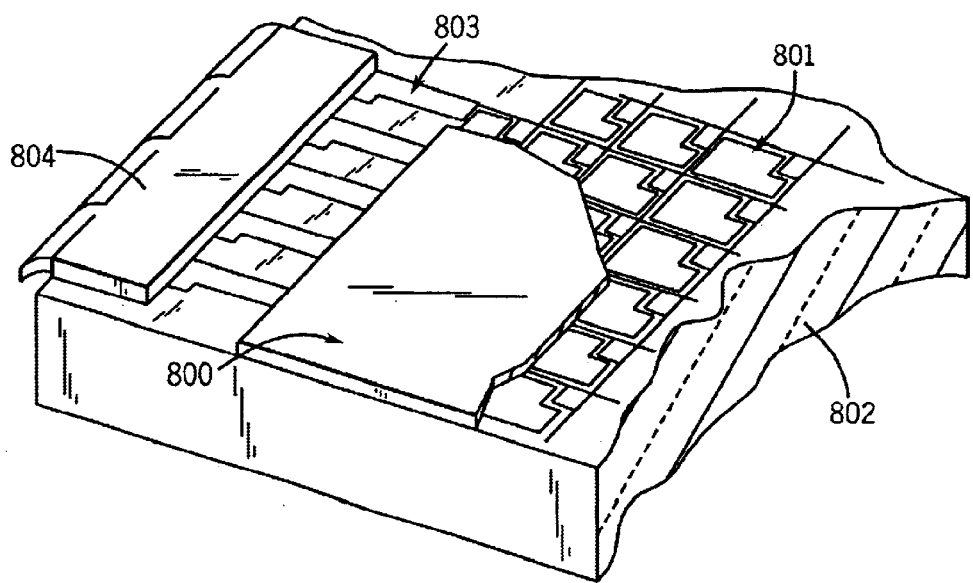
FIGS. 9a and 9b are schematic diagrams of and flow charts relating to one exemplary embodiment of a flat-panel detector.

FIG. 9a shows one example of a flat-panel x-ray detector. The flat panel detector includes an Amorphous Silicon Array 801 which is made of amorphous silicon diodes and thin-film transistors (TFTs). Utilizing thin film technology similar to that used in the fabrication of integrated circuits, layers of amorphous silicon and various metals and insulators are deposited on a glass substrate 802 to form an Amorphous Silicon Array 801 of photodiodes and a TFTs matrix, as well as the interconnections 803, and the contacts 804 on the edges of the panel. The scintillator 800, which converts x-ray photons into visible light photons, is made of Cesium Iodide and is deposited directly on top of the Amorphous Silicon Array 801.

Another common flat-panel detector uses a selenium array which is made of selenium diodes and thin-film transistors. The use of selenium obviates the need for a scintillator 800 because the selenium generates signals in response to the x-ray radiation directly.

Also, research is being conducted relating to polymers with properties that can be used to generate signals in response to radiation. Conceivably, these polymers, and other organic-based materials, may eventually be used to form flat panel detectors as well.

Figure 9B:
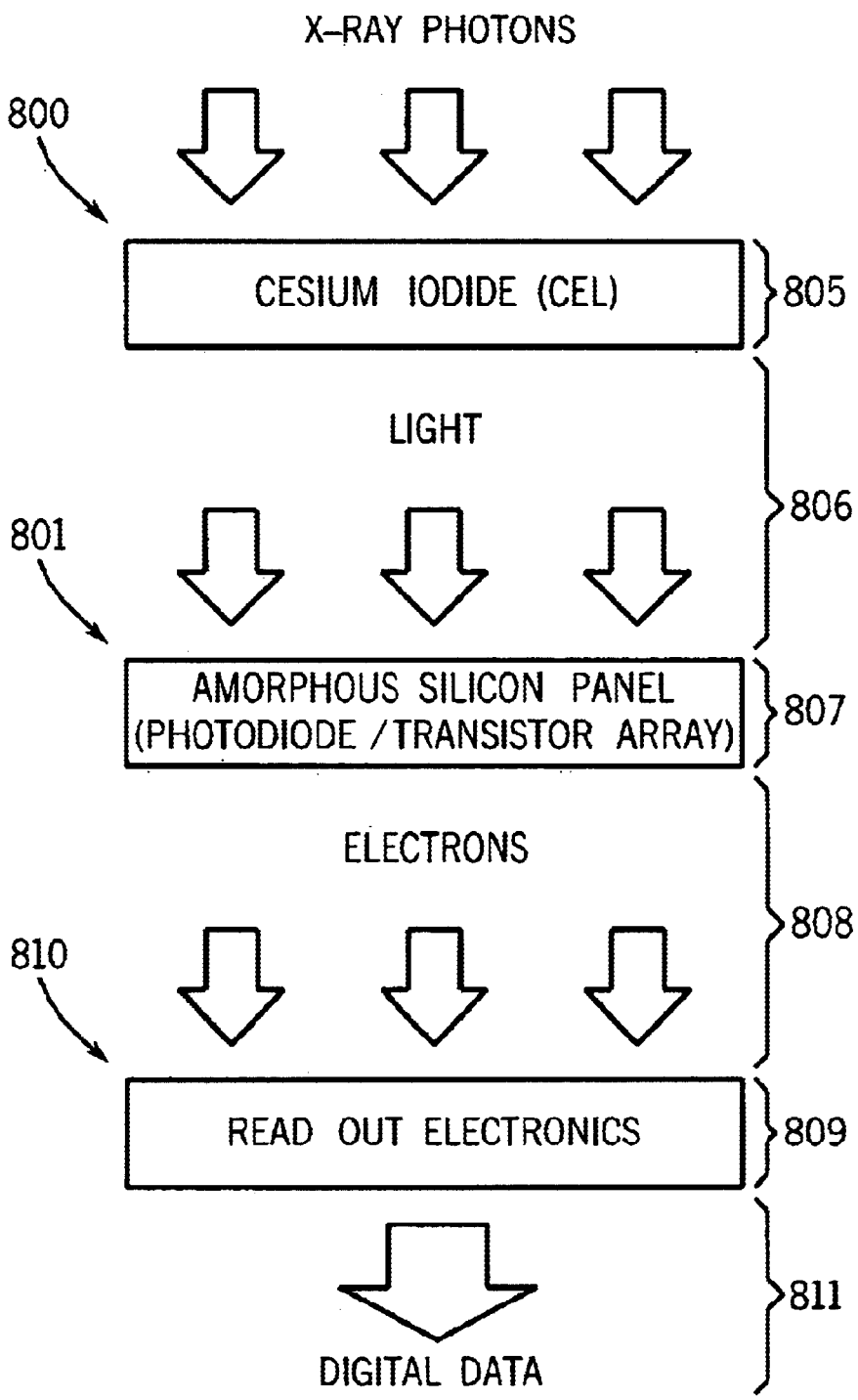

FIG. 9b shows how the flat-panel detector of FIG. 9a operates to detect signals. The cesium iodide (CsI) scintillator 800 absorbs x-ray photons, converting 805 their energy into light photons emission. This light is then channeled 806 toward the amorphous silicon photodiode array 801 where it causes the charge of each photodiode to be depleted 807 in proportion to the light it receives. Each of these photodiodes is a picture element (pixel); the spatial sampling of the image, which is the first step in image digitization, is thus performed exactly where the image is formed. The electronic charge required to recharge 808 each photodiode is then read 809 by electronics 810 and converted 811 into digital data that can then be used.

The term "direction of movement" as used herein refers to a line, which line can potentially extend in more than one direction. The line is defined by adjacent positions of individual images that can be used to form a pasted image. While an x-ray detector may move from one position to another in a non-linear fashion, the overall direction of movement between two subsequent positions is necessarily linear.

Also, the field of view in a direction of movement is defined as the field of view along that line. For instance, a detector with a rectangular input field would have a field of view equal to the length of the detector in the direction of movement. Also, a detector with a circular input field would have a field of view that is equal to its diameter, which is typically constant in all directions.

The invention has been described with reference to various specific and illustrative embodiments and techniques. However, it should be understood that many variations and modifications may be made while remaining within the spirit and scope of the invention. For instance, the focal point of x-ray source 2 need not bisect the area to be imaged. Also, an area to be imaged might be longer than a length of the field of view of the x-ray detector in more than one direction.

What is claimed is:

1. A method for obtaining a view of an area of a subject that is larger than a field of view used by an x-ray detector by obtaining at least two images, the at least two images having an area of overlap, the method comprising:
   determining a location of an identified structure; and
   setting the at least two images in locations that avoid placing the identified structure in the area of overlap of the at least two images, the at least two images being capable of being used to obtain an image with a field of view larger than that used by the x-ray detector to collect the at least two images.

2. The method of claim 1, wherein the identified structure is a structure that tends to move between collection of subsequent images.

3. The method of claim 2, wherein the identified structure is selected from a group consisting of a heart, a diaphragm, a chest wall, and a bowel gas.

4. The method of claim 1, wherein the identified structure is a structure that is dose-sensitive.

5. The method of claim 4, wherein the identified structure is selected from a group consisting of a thyroid, gonads, breast tissue, and photographic film.

6. The method of claim 1, wherein the x-ray detector is a flat-panel x-ray detector.

7. The method of claim 1, wherein determining the location of the identified structure comprises receiving a user input.

8. The method of claim 1, wherein determining the location of the identified structure comprises determining a likely position of the identified structure based on information relating to characteristics of the subject or type of procedure.

9. A system configured to obtain a view of an area of a subject that is larger than a field of view used by an x-ray detector by obtaining at least two images, the at least two images having an area of overlap, the system comprising:
- an x-ray source;
- the x-ray detector;
- a computational unit configured to:
  - receive a location of an identified structure; and
  - determine positions of at least two images to be collected by the x-ray detector when x-rays are emitted by the x-ray source such that the at least two images are in locations that avoid placing the identified structure in the area of overlap of the at least two images;
- a position change controller coupled to the computational unit; and
- an x-ray detector position change actuator configured to change a relative position between the subject and the x-ray detector in response to the position change controller such that the x-ray detector can collect images in the positions determined by the computational unit.

10. The system of claim 9, wherein the identified structure is a structure that tends to move between collection of subsequent images.

11. The system of claim 10, wherein the identified structure is selected from a group consisting of a heart, a diaphragm, a chest wall, and a bowel gas.

12. The system of claim 9, wherein the identified structure is a structure that is dose-sensitive.

13. The system of claim 12, wherein the identified structure is selected from a group consisting of a thyroid, gonads, breast tissue, and photographic film.

14. The system of claim 9, wherein the x-ray detector is a flat-panel x-ray detector.

15. The system of claim 9, further comprising a processor configured to form a pasted image from the at least two images.

16. The system of claim 15, further comprising a display configured to display the pasted image.

17. The system of claim 9, further comprising a network interface configured to allow data to be transferred.

18. The system of claim 17, wherein the data allowed to be transferred includes data selected from a group consisting of individual images, a pasted image, subject file data, and a billing record.

19. A computer readable medium containing a control program configured to facilitate obtaining a view of an area of a subject that is larger than a field of view used by an x-ray detector by obtaining at least two images, the at least two images having an area of overlap, the program comprising:
- a program feature to receive an input of a location of an identified structure; and
- a program feature to determine positions needed of at least two images collected by an x-ray detector such that the at least two images are in locations that avoid placing the identified structure in the area of overlap of the at least two images.

20. The computer readable medium of claim 19, herein the program feature to receive an input of a location of the identified structure is configured to receive a user input indicative of the location of the user input.

21. The computer readable medium of claim 19, wherein:
- the program feature to receive an input of a location of the identified structure is configured to receive an input of information relating to characteristics of the subject or type of procedure; and
- the program feature to determine positions needed of the at least two images is configured to determine the positions based on a likely position of the identified structure based on the information.

22. A method for obtaining a view of an area of a patient that is larger than a field of view used by an x-ray detector by obtaining at least two images, the at least two images having an area of overlap, the method comprising:
- determining a location of an organ; and
- setting the at least two images in locations that avoid placing the organ in the area of overlap of the at least two images, the at least two images being capable of being used to obtain an image with a field of view larger than that used by the x-ray detector to collect the at least two images.

23. The method of claim 22, wherein the organ is an organ that tends to move between collection of subsequent images.

24. The method of claim 22, wherein the organ is an organ that is dose-sensitive.

25. A system configured to obtain a view of an area of a subject that is larger than a field of view used by an x-ray detector by obtaining at least two images, the at least two images having an area of overlap, the system comprising:
- an x-ray source;
- the x-ray detector configured to receive x-rays from the x-ray source; and
- a processing circuit configured to receive an input representative of a location of an organ and to determine positions of at least two images to be collected by the x-ray detector when x-rays are emitted by the x-ray source such that the at least two images are in locations that avoid placing the organ in the area of overlap of the at least two images;
- wherein positions of the x-ray detector are controlled based on the positions determined by the processing circuit.

26. The system of claim 25, wherein the organ is an organ that tends to move between collection of subsequent images.

27. The system of claim 26, wherein the organ is selected from a group consisting of a heart, a diaphragm, a chest wall, and a bowel gas.

28. The system of claim 25, wherein the organ is an organ that is dose-sensitive.

29. The system of claim 28, wherein the organ is selected from a group consisting of a thyroid, gonads, and breast tissue.

30. The system of claim 25, wherein the x-ray detector is a flat-panel x-ray detector.

31. The system of claim 25, further comprising a processor configured to form a pasted image from the at least two images.

32. The system of claim 31, further comprising a display configured to display the pasted image.

33. The system of claim 25, further comprising a network interface configured to allow data to be transferred.

34. The system of claim 33, wherein the data allowed to be transferred includes data selected from a group consisting of individual images, a pasted image, subject file data, and a billing record.

35. A computer readable medium containing a control program for a processor configured to facilitate obtaining a view of an area of a subject that is larger than a field of view used by an x-ray detector by obtaining at least two images, the at least two images having an area of overlap, the program comprising:
- a program feature configured to receive an input of a location of an organ; and a program feature configured to determine positions needed of at least two images collected by an x-ray detector such that the at least two images are in locations that avoid placing the organ in the area of overlap of the at least two images.

36. The computer readable medium of claim 35, wherein the program feature configured to receive an input of a location of the organ is configured to receive a user input indicative of the location of the organ.

37. The computer readable medium of claim 35, wherein:
the program feature configured to receive an input of a location of the organ is configured to receive an input of information relating to at least one of a characteristic of the subject and type of procedure; and
the program feature configured to determine positions needed of the at least two images is configured to determine the positions based on a likely position of the organ of the subject based on the information.

38. A method for obtaining a view of an area of a subject that is larger than a field of view used by an x-ray detector by obtaining at least two individual images, the at least two images having an area of overlap, the method comprising:
receiving information relating to a location of an identified structure; and
determining positions of images collected by an x-ray detector which can be pasted together to form an image of the subject which includes the identified structure and has a field of view larger than any of the individual images, the positions determined so that the identified structure is not in an area of overlap of the individual images.

39. The method of claim 38, further comprising pasting the individual images together.

40. The method of claim 38, wherein the identified structure is a structure that tends to move between collection of subsequent images.

41. The method of claim 38, wherein the identified structure is selected from a group consisting of a heart, a diaphragm, a chest wall, and a bowel gas.

42. The method of claim 38, wherein the identified structure is a structure that is dose-sensitive.

43. The method of claim 38, wherein the identified structure is selected from a group consisting of a thyroid, gonads, breast tissue, and photographic film.

44. The method of claim 38, wherein receiving information relating to a location of an identified structure comprises receiving a user input.

45. The method of claim 44, wherein receiving a user input comprises receiving a user input that indicates the position of the identified structure.

46. The method of claim 38, wherein determining the location of the identified structure comprises determining a likely position of the identified structure based on information relating to characteristics of the subject or type of procedure.

47. The method of claim 38, further comprising controlling positions of the x-ray detector with a processing circuit based on the positions which are determined.

* * * * *

UNITED STATES PATENT AND TRADEMARK OFFICE
CERTIFICATE OF CORRECTION

PATENT NO. : 6,895,076 B2
DATED : May 17, 2005
INVENTOR(S) : Mattew A. Halsmer and Richard J. Warp It is certified that error appears in the above-identified patent and that said Letters Patent is hereby corrected as shown below:

Column 15,
Line 58, please replace "herein" with -- wherein --.

Signed and Sealed this

Second Day of August, 2005

JON W. DUDAS
*Director of the United States Patent and Trademark Office*